United States Patent [19]

Kelman

[11] Patent Number: 4,504,264

[45] Date of Patent: Mar. 12, 1985

[54] APPARATUS FOR AND METHOD OF REMOVAL OF MATERIAL USING ULTRASONIC VIBRATION

[76] Inventor: Charles D. Kelman, 269-70 Grand Central Pkwy., Floral Park, N.Y. 11005

[21] Appl. No.: 422,387

[22] Filed: Sep. 24, 1982

[51] Int. Cl.³ .......................... A61B 17/20; A61B 5/18
[52] U.S. Cl. ......................................... 604/22; 604/27; 604/28; 604/35
[58] Field of Search .................. 128/24 A, 303 C, 305; 604/22, 27, 28, 35, 46; 433/118, 119

[56] References Cited

U.S. PATENT DOCUMENTS

| | | | |
|---|---|---|---|
| 3,433,226 | 3/1969 | Boyd | 604/22 |
| 3,526,219 | 9/1970 | Balamuth | 433/119 |
| 3,589,363 | 6/1971 | Banko et al. | 128/276 |
| 3,805,793 | 4/1974 | Wright | 604/22 |
| 3,902,495 | 9/1975 | Weiss et al. | 604/22 |
| 3,942,519 | 3/1976 | Shock | 128/24 A |
| 4,428,748 | 1/1984 | Peyman | 604/22 |

Primary Examiner—C. Fred Rosenbaum
Assistant Examiner—J. Kruter
Attorney, Agent, or Firm—Henry Sternberg

[57] ABSTRACT

A hand-held surgical instrument for fragmentation and removal of animal tissue such as a cataract has a working tip which in addition to being longitudinally vibrated is laterally oscillated to enhance the operation thereof. Also, the method of laterally oscillating the working tip in the range of about 5 degrees to about 60 degrees, longitudinally vibrating the tip ultrasonically, supplying treatment fluid to the region adjacent to the working tip and withdrawing the suspended particles of the cataract in the fluid.

7 Claims, 2 Drawing Figures

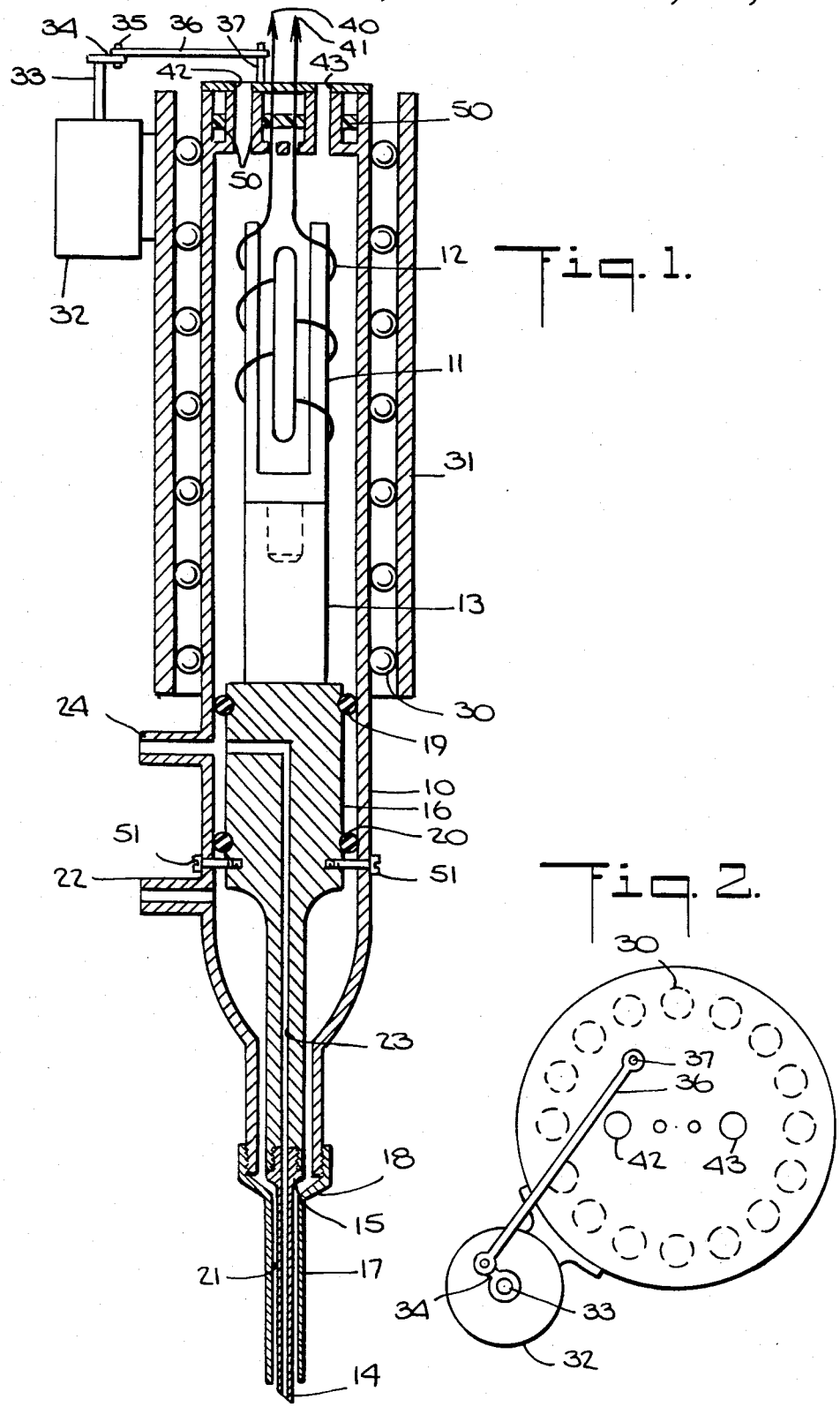

APPARATUS FOR AND METHOD OF REMOVAL OF MATERIAL USING ULTRASONIC VIBRATION AND LATERAL OSCILLATION

This invention relates to material-removal apparatus and methods, and, more particularly, to an instrument having an operative working tip vibrating at high frequency and at small amplitudes for breaking apart and removing material from relatively inaccessible places and methods for its use. The present apparatus is particularly advantageous when employed as a surgical instrument for breaking apart and the removal of unwanted tissue, for example, a cataract from a human eye.

Apparatus of this type is described and claimed in my U.S. Pat. No. 3,589,363 issued June 29, 1971. Improved apparatus of this type is described in my publication "PHACO-EMULSIFICATION and ASPIRATION," published in the American Journal of Ophthalmology, Vol. 67, No. 4, April, 1969.

While the previously described apparatus is satisfactory, I have found that the speed with which the cataract can be fragmented and removed can be considerably increased in accordance with the present invention.

It is an object of the present invention, therefore, to avoid one or more of the limitations of such prior apparatus and methods.

It is another object of the invention to provide a new and improved apparatus for and method of breaking apart and removal of animal tissue and the like which accomplishes such fragmentation and removal in a shorter period of time than was heretofore possible.

It is another object of the invention to provide a new and improved apparatus for and method of breaking apart and removal of a cataract from an eye which accomplishes such fragmentation and removal in a shorter period of time than was heretofore possible.

In accordance with the invention, apparatus for the breaking apart and removal of animal tissue and the like from an enclosed area comprises an elongated working tip adapted to have one end placed directly against the tissue and capable of supporting ultrasonic vibrations. The apparatus includes means for applying longitudinal ultrasonic vibrations to the working tip, means for supporting the working tip for lateral rotation, and means for laterally rotating the working tip. The apparatus also includes means for supplying a treatment fluid to bathe the tissue in the region adjacent the working tip and means adjacent the working tip for withdrawing the suspension of particles of the tissue in the fluid resulting from ultrasonic vibration of the working tip.

Also in accordance with the invention, a method for the breaking apart and removal of animal tissue and the like from an enclosed area, employing an elongated working tip comprises the simultaneous steps of applying ultrasonic vibrations to the working tip in contact with the tissue, supplying a treatment fluid to bathe the tissue in the region adjacent the working tip, withdrawing the suspension of particles of the tissue in the fluid so that the pressure within the enclosed area is controlled, and laterally rotating the working tip.

For a better understanding of the present invention, together with other and further objects thereof, reference is made to the following description, taken in connection with the accompanying drawings, and its scope will be pointed out in the appended claims.

Referring now to the drawings:

FIG. 1 is a cross-sectional view, partly schematic, of apparatus constructed in accordance with the present invention;

FIG. 2 is an end view, partly schematic, of the FIG. 1 apparatus.

Referring now more particularly to FIG. 1 of the drawings, apparatus for the breaking apart and removal of animal tissue and the like from an enclosed area and, more particularly, a surgical instrument adapted to be held in the hand and moved freely during operative use, comprises a casing 10 of, for example, stainless steel. The instrument also comprises transducer means 11 supported within the casing 10 for generating high frequency mechanical vibrations upon excitation with a high frequency alternating-current electrical signal. The transducer 11 preferably is a magnetostrictive transducer with an electrical coil 12 wound about each leg in such a manner as to develop in-phase longitudinal mechanical vibrations in both legs. The instrument includes a connecting body 13 of, for example, titanium, attached to another connecting body 16 and which form an acoustic impedance transformer for increasing the amplitude of the longitudinal vibrations of the transducer 11 for application to the operative tool or working tip 14 of the instrument.

The working tip 14 is at least partially external of the casing 10 and is supported thereby and is coupled to the transducer means 11 to be longitudinally vibrated thereby. The working tip 14 preferably is an elongated, hollow tip capable of supporting ultrasonic vibrations and having a beveled end adapted to be placed against the tissue to be removed. The working tip 14 preferably is an interchangeable cutting tip of titanium having a base portion 15 in threaded engagement with one end of the connecting body 16.

The tip 14 preferably is surrounded by a silicon sleeve 17 supported on a reduction housing 18 in threaded engagement with the casing 10.

The connecting body 16 has disposed thereon two elastomeric O-rings 19, 20 which provide fluid-tight seals between the connecting body 16 and the casing 10. A plurality of screws 51 are disposed around the axis of the casing 10 for preventing longitudinal displacement (other than vibrational) or rotational movement of the vibratory structure within the casing and also for radially centering the vibratory structure within the casing.

Means including the sleeve 17 around the tip 14 forms a first fluid passage 21 between the tip 14 and a point remote therefrom. Means for supplying fluid to the passage 21 comprises an inlet 22 to which a treatment fluid supply (not shown) may be coupled.

means comprising the connecting body 16 is coupled to the tip 14 for providing a second fluid passage 23 between the hollow interior of the tip 14 and a point remote therefrom. Means for applying a suction force to the passage 23 comprises an outlet 24 to which a suction pump (not shown) may be coupled.

The apparatus also includes means for supporting the working tip 14 for lateral rotation. The supporting means includes the casing 10 surrounded by ball bearings 30 and an outer sleeve 31, which may be hand-held.

There is mounted on the sleeve 31 a motor 32 for laterally rotating the casing 10 and the working tip 14 and preferably for oscillating the working tip within the range from about 5 degrees to about 60 degrees at a frequency in the range of approximately 1 cycle per second to approximately 10 cycles per second.

Referring now more particularly to FIG. 2, the output shaft 33 of the motor 32 is fixedly connected to a short rotatable arm 34 having a rotatable connection 35 to a longer arm 36 which, in turn, is pivotally connected to a leg 37 extending from the end of the casing 10.

The apparatus also includes electrical input terminals 40, 41 for applying a suitable electrical signal to the magnetostrictive transducer 11. A cooling water inlet 42 and a cooling water outlet 43 for circulating cooling water inside the casing 10 in the region around the magnetostrictive transducer 11 and connecting body 13 are provided and are sealed by the "O-ring" 19 and by a fluid-tight grommet 50.

Suitable apparatus (not shown) including a suction pump, a treatment fluid supply, an oscillator for applying an electrical signal to the vibratory structure and control apparatus therefor may be of conventional construction, for example, as described in U.S. Pat. No. 3,589,363. Additionally, a conventional 60 cycle, alternating-current supply circuit may be utilized to energize the motor 32.

Considering now the operation of the instrument, when an electrical signal having a frequency of, for example, 40,000 cycles is applied to the coil 12 around the magnetostrictive transducer 11, the transducer 11 vibrates longitudinally at 40,000 cycles per second, thereby vibrating the connecting bodies 13, 16 and the working tip 14. Treatment fluid is supplied through inlet 22 and fluid passage 21 to bathe the tissue in the region around the working tip 14. Suction is applied through inlet 24 and passage 23 to the working tip 14 to withdraw the fragmented tissue.

At the same time the output shaft of the motor 32 rotates at, for example, 60 revolutions per minute. In order to accomplish this, the motor may include suitable gearing and/or electronic circuitry.

Rotation of the shaft 33, causes rotation of the arm 34. The arm 36 pivots at connection 35 and causes the leg 37 to oscillate laterally at a frequency in the range of approximately 1 cycle per second to approximately 10 cycles per second supported by the ball bearings 30 within sleeve 31 which is held by the surgeon's hand. This causes lateral oscillation of the working tip 14 while the latter is vibrating longitudinally. The relatively low frequency lateral oscillating motion of the working tip, superimposed on the relatively high frequency longitudinal vibrational movement thereof results in fragmentation and removal of tissue, such as a cataract in an eye, in a shorter period of time than was heretofore possible.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A surgical instrument adapted to be held in the hand and moved freely during operative use comprising:
   a casing;
   transducer means supported within said casing for generating high frequency mechanical vibrations upon excitation with a high frequency alternating-current electrical signal;
   an operative tool at least partially external of said casing and supported thereby and coupled to said transducer means to be longitudinally vibrated thereby;
   means for supporting said casing for lateral rotation;
   means for laterally oscillating said csing and thereby laterally oscillating said operative tool;
   a first fluid passage extending through said casing and in surrounding relation to at least a portion of said operative tool; and
   a second fluid passage formed in part internally of said operative tool and extending into said casing, one of said passages being adapted to conduct a fluid to said operative tool and the other of said passages being adapted to withdraw fluid from the region adjacent said operative tool.

2. An instrument in accordance with claim 1 in which said means for supporting said casing for lateral rotation comprises an outer cylindrical sleeve and rotatable bearings therein.

3. A method for the breaking apart and removal of a cataract from an eye employing a working tip comprising the steps of:
   applying ultrasonic vibrations through said working tip in contact with said cataract;
   supplying a treatment fluid to bathe the eye in the region adjacent said working tip;
   withdrawing the suspension of particles of said cataract in said fluid so that the pressure within the eye is controlled; and
   laterally oscillating the working tip within the range from about 5 degrees to about 60 degrees at a frequency in the range of approximately 1 cycle per second to approximately 10 cycles per second.

4. A method in accordance with claim 3 in which the step of applying ultrasonic vibrations to the working tip comprises applying vibrations at a frequency of approximately 40,000 cycles per second.

5. Apparatus for breaking apart and removal of animal tissue from an enclosed area comprising;
   an elongated working tip adapted to have one end placed directly against the tissue and capable of supporting ultrasonic vibrations;
   means for applying longitudinal ultrasonic vibrations to said working tip;
   means for laterally oscillating said working tip within he range from about 5 degrees to about 60 degrees;
   means for supplying a treatment fluid to bathe said tissue in the region adjacent said working tip; and
   means for withdrawing the suspension of particles of said tissue in said fluid adjacent said working tip resulting from ultrasonic vibrations and lateral oscillation of said working tip.

6. Apparatus for breaking apart and removal of animal tissue from an enclosed area comprising:
   an elongated working tip adapted to have one end placed directly against the tissue and capable of supporting ultrasonic vibrations;
   means for applying longitudinal ultrasonic vibrations to said working tip;
   means for laterally oscillating said working tip at a frequency in the range of approximately 1 cycle per second to approximately 10 cycles per second;
   means for supplying a treatment fluid to bathe said tissue in the region adjacent said working tip; and
   means for withdrawing the suspension of particles of said tissue in said fluid adjacent said working tip resulting from ultrasonic vibrations and lateral oscillation of said working tip.

7. Apparatus in accordance with either of claims 5 or 6 in which said means for applying ultrasonic vibrations generates said vibrations at a frequency of approximately 40,000 cyles per second.

* * * * *